(12) United States Patent
Schneider et al.

(10) Patent No.: US 8,058,369 B2
(45) Date of Patent: Nov. 15, 2011

(54) METHOD FOR OPERATING BUBBLE COLUMN REACTOR FOR THE OLIGOMERIZATION OF ETHYLENE

(75) Inventors: Richard Schneider, Uffing (DE); Peter M. Fritz, Unterhaching (DE); Sebastian Muschelknautz, Munich (DE); Heinz Bölt, Wolfratshausen (DE); Talal Ali, Riyadh (SA); Fuad Mosa, Riyadh (SA)

(73) Assignees: Saudi Basic Industries Corporation, Riyadh (SA); Linde AG, Munich (DE)

( * ) Notice: Subject to any disclaimer, the term of this patent is extended or adjusted under 35 U.S.C. 154(b) by 394 days.

(21) Appl. No.: 12/083,806

(22) PCT Filed: Sep. 6, 2006

(86) PCT No.: PCT/EP2006/008652
§ 371 (c)(1), (2), (4) Date: Apr. 3, 2009

(87) PCT Pub. No.: WO2007/045306
PCT Pub. Date: Apr. 26, 2007

(65) Prior Publication Data
US 2009/0214405 A1    Aug. 27, 2009

(30) Foreign Application Priority Data

Oct. 20, 2005 (EP) ................................ 05022865

(51) Int. Cl.
*C08F 2/00* (2006.01)

(52) U.S. Cl. ............ 526/74; 261/19; 261/20; 261/23.1; 261/75; 261/76; 562/413; 562/414; 562/415; 562/416

(58) Field of Classification Search ............... 422/188, 422/189, 231, 224, 230; 261/19, 20, 23.1, 261/75, 76; 562/413, 414, 415, 416; 526/74
See application file for complete search history.

(56) References Cited

U.S. PATENT DOCUMENTS

| | | | |
|---|---|---|---|
| 3,004,016 A | | 10/1961 | Hawkins |
| 4,994,534 A | * | 2/1991 | Rhee et al. ................ 526/88 |
| 5,019,268 A | | 5/1991 | Rogalla |
| 5,200,477 A | * | 4/1993 | Baker et al. ............... 526/74 |
| 6,117,399 A | * | 9/2000 | Jorgensen et al. ........ 422/142 |
| 7,078,439 B2 | * | 7/2006 | Odueyungbo et al. .... 518/700 |
| 2003/0129110 A1 | | 7/2003 | Steynberg |
| 2007/0020170 A1 | * | 1/2007 | Khattaty et al. ........ 423/573.1 |

FOREIGN PATENT DOCUMENTS
GB           1250222 A     10/1971
* cited by examiner

*Primary Examiner* — Walter Griffin
*Assistant Examiner* — Huy-Tram Nguyen
(74) *Attorney, Agent, or Firm* — Kramer Levin Naftalis & Frankel LLP

(57) ABSTRACT

The present invention relates to a bubble column reactor comprising a column reactor having a sparger plate dividing the column reactor into a top reaction compartment and a bottom compartment, characterized in that an inlet and outlet line for introducing and disposing a flushing medium are connected to the bottom compartment; and an operation method thereof.

6 Claims, 1 Drawing Sheet

METHOD FOR OPERATING BUBBLE COLUMN REACTOR FOR THE OLIGOMERIZATION OF ETHYLENE

Figure 1:
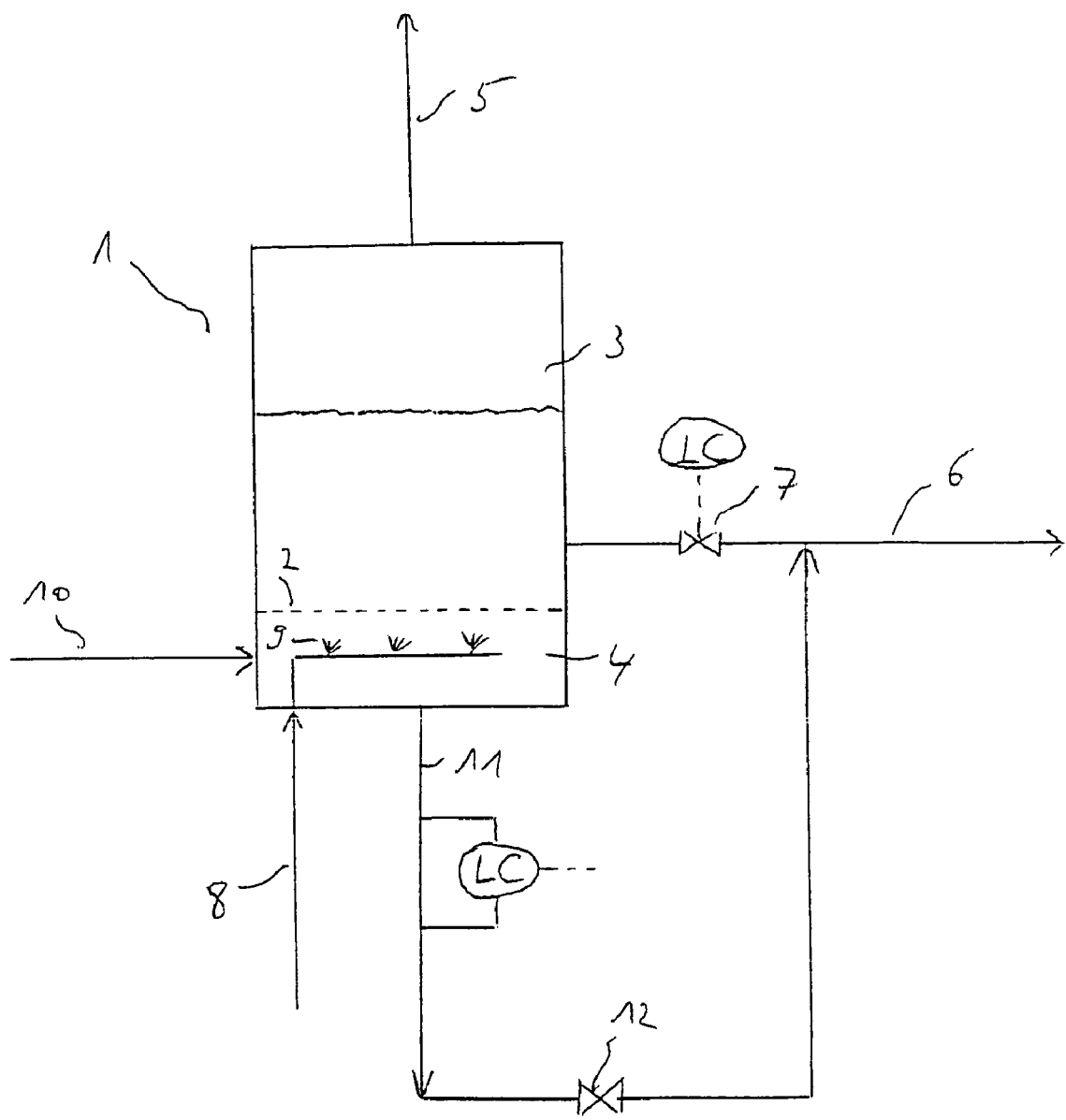

The present invention relates to a bubble column reactor comprising a column reactor having a sparger plate dividing the column reactor into a top reaction compartment and a bottom compartment, and to an operation method thereof.

Bubble column reactors are widely known in the art. A bubble column reactor is, for example, utilized for the oligomerization of ethylene to form linear alpha-olefins (LAO). Such a bubble column reactor comprises a column reactor which is divided by a sparger plate into an upper reaction compartment and a bottom compartment. Via the bottom compartment a gaseous feed of monomer(s) is introduced into the column reactor and passes through the sparger plate and into the homogenous solution comprising monomer(s), solvent and catalyst in the upper compartment to then form linear alpha-olefins. From the top of the upper reaction compartment gaseous products and the like are removed. Further, a line is provided to remove a liquid mixture comprising solvent, catalyst, dissolved monomer(s) and linear alpha-olefins.

In conventional bubble column reactors there is a problem that weeping of the sparger plate may occur which may lead to a filling of the bottom compartment. This may often have the disadvantages that a potential mechanical damage may occur, the gas distribution above the sparger plate may be disturbed and plugging of the bottom compartment and outlet lines due to reactive material below the sparger plate may take place.

It is therefore an object of the present invention to provide a bubble column reactor and an operation method thereof which overcome the drawbacks of the prior art. Especially, a bubble column reactor and a method shall be provided wherein the consequences of weeping of the sparger plate in the bubble column reactor may be avoided or at least controlled.

This object is achieved in that an inlet and an outlet line for introducing and disposing a flushing medium are connected to the bottom compartment.

Preferably, the outlet line is connected to piping or equipment downstreams of the column reactor.

In one embodiment, the flushing medium is selected from the group consisting of linear alpha olefins or aromatics.

The object is further achieved by a method for operating a bubble column reactor comprising a column reactor having a sparger plate dividing the column reactor into a top reaction compartment and a bottom compartment, wherein flushing medium is introduced into and disposed of the bottom compartment via inlet line and outlet line, respectively.

Preferably, the flushing medium is transferred from the outlet line to piping or equipment downstreams of the column reactor.

Even preferred, a gaseous feed of monomer(s) is introduced into the bottom compartment.

Finally, in a most preferred embodiment, the bottom compartment is continuously flushed.

Surprisingly, it was found that disadvantages of conventional bubble column reactors may be overcome in that the bottom compartment of the column reactor is, preferably continuously, flushed with a flushing medium. By flushing the bottom compartment material (caused by weeping of the sparger plate), being reactive or un-reactive, may be disposed of the bottom compartment. Preferably, the flushed medium is transferred to pipings or equipment which are located downstreams of the column reactor. Even preferred, a control unit is provided for the inventive bubble column reactor controlling the inlet and outlet rates of the flushing medium into and out of the bottom compartment, and also preferably controlling the discharge rate of outlet streams leaving the column reactor above the sparger plate.

Additional advantages and features of the inventive bubble column reactor and its operation method are further illustrated with reference to the accompanying drawing, wherein FIG. 1 illustrates a schematic diagram of an inventive bubble column reactor.

According to FIG. 1, an inventive bubble column reactor is shown having a sparger plate 2 dividing a column reactor 1 into a top reaction compartment 3 and a bottom compartment 4. As can be seen, the top reaction compartment 3 is at least partly filled with a homogenous mixture comprising solvent, monomer(s), catalyst and already prepared linear alpha-olefins. Via line 5 gaseous components may be removed from the top reaction compartment 3 which may comprise solvent, monomer(s) and gaseous linear alpha-olefins, for further processing. Further, line 6 having a valve 7 is provided to remove a liquid mixture comprising solvent, dissolved monomer(s), catalyst and liquid linear alpha-olefins from the column reactor 1 for further processing.

Via feed line 8 a gaseous feed of monomer(s) may be introduced into the bottom compartment 4 and may be distributed via one or more nozzles 9 or the like. The distributed gaseous feed may then pass through the sparger plate 2 and distribute into the homogenous mixture in the top reaction compartment.

The column reactor 1 additionally comprises an inlet line 10 for introducing flushing medium into the bottom compartment 4. The flushing medium may be disposed of the bottom compartment 4 via an outlet line 11 having a valve 12. The outlet line 11 is, according to the embodiment shown in FIG. 1, connected to further piping or equipment downstreams of the column reactor 1 to be further processed.

A control unit (not shown) may be also provided for controlling the inlet and outlet rate of the flushing medium into and out of the bottom compartment 4, and for controlling the valve 7 and other equipment not shown.

Preferably, the bottom column is continuously flushed with flushing medium. Even preferred, the flushing medium is spread over the substantially whole bottom compartment to provide an intensive and sufficient flushing thereof.

The inventive bubble column reactor or its operation method may not avoid weeping of the sparger plate, but overcomes the consequences related thereto, such as potential mechanical damage, disturbance of the gas distribution above the sparger plate and plugging of the bottom compartment and outlet lines due to material below the sparger plate.

The features disclosed in the foregoing description, in the claims and in the drawing may, both separately and in any combination thereof, be material for realizing the invention in diverse forms thereof.

The invention claimed is:

1. A method for operating a bubble column oligomerization reactor comprising a column reactor having a sparger plate dividing the column reactor into a top reaction compartment and a bottom compartment, wherein a gaseous monomer is fed into said bottom compartment and flows through said sparger plate into said top reaction compartment, comprising introducing a flushing medium into said bottom compartment via an inlet line and discharging the flushing medium from said bottom compartment via an outlet line.

2. The method according to claim 1, wherein the flushing medium is transferred from the outlet line to pipings or equipment downstream of the column reactor.

3. The method according claim 1, wherein the bottom compartment is continuously flushed.

4. The method according to claim 1, wherein the flushing medium is selected from the group consisting of linear alpha olefins or aromatics.

5. The method according to claim 2, wherein the flushing medium is selected from the group consisting of linear alpha olefins or aromatics.

6. The method according to claim 3, wherein the flushing medium is selected from the group consisting of linear alpha olefins or aromatics.

* * * * *